United States Patent [19]

Weller, III et al.

[11] Patent Number: 4,512,988

[45] Date of Patent: Apr. 23, 1985

[54] ACYLAMINO OXO OR HYDROXY SUBSTITUTED ALKYLAMINO THIAZINES AND THIAZEPINES

[75] Inventors: Harold N. Weller, III; Eric M. Gordon, both of Pennington; Donald S. Karanewsky, East Windsor; Denis E. Ryono, Princeton, all of N.J.

[73] Assignee: E. R. Squibb & Sons, Inc., Princeton, N.J.

[21] Appl. No.: 585,058

[22] Filed: Mar. 1, 1984

[51] Int. Cl.³ .................. C07D 279/06; C07D 285/36; A61K 31/55; A61K 31/54
[52] U.S. Cl. .................................. 514/211; 260/244.4; 260/245.7; 260/245.5; 260/330; 260/239.3 R; 260/239.3 B; 544/54; 514/226
[58] Field of Search ............... 260/244.4, 245.7, 245.5, 260/330, 239.3 R, 239.3 B; 544/54; 424/244, 246, 184

[56] References Cited

U.S. PATENT DOCUMENTS 4,329,473 5/1982 Almquist et al. .................. 546/281
4,460,579 7/1984 Karanewsky ....................... 424/200
4,470,973 9/1984 Natarajan et al. .................. 424/177

FOREIGN PATENT DOCUMENTS 68173 1/1983 European Pat. Off. .

OTHER PUBLICATIONS

Meyer et al., "Angiotensin Converting Enzyme Inhibitors . . . ", *J. Med. Chem.*, 1982, pp. 996–999.

*Primary Examiner*—John M. Ford
*Attorney, Agent, or Firm*—Lawrence S. Levinson; Stephen B. Davis

[57] ABSTRACT

Compounds of the formula $$R-NH-X-\underset{R_1}{\overset{}{CH}}-\overset{O}{\underset{}{C}}-OR_2$$

wherein R is 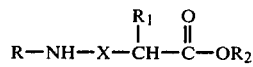

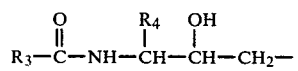

and X is an oxo substituted thiazine or thiazepine are disclosed. These compounds possess angiotensin converting enzyme inhibition activity and are thus useful as hypotensive agents.

11 Claims, No Drawings

ACYLAMINO OXO OR HYDROXY SUBSTITUTED ALKYLAMINO THIAZINES AND THIAZEPINES

BACKGROUND OF THE INVENTION

Patchett et al. in European Patent Application 68,173 disclose that various substituted carboxyalkylamino perhydro-1,4-thiazepin-5-ones and perhydro-1,4-thiazocin-5-ones possess angiotensin converting enzyme inhibition activity.

Meyer et al., "Angiotensin Converting Enzyme Inhibitors:Modifications Of A Tripeptide Analogue", J. Med. Chem., 1982, 25, 996–999, disclose the synthesis and angiotensin converting enzyme inhibition activity of compounds of the formula

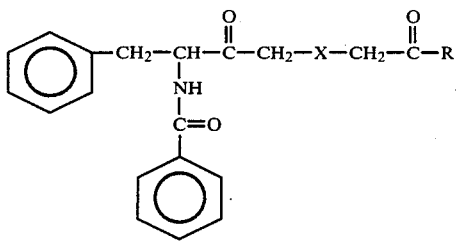

wherein X can be NH and R can be L-proline.

Almquist et al. in U.S. Pat. No. 4,329,473 disclose oxoalkanoic acid derivatives of L-proline as angiotensin converting enzyme inhibitors.

SUMMARY OF THE INVENTION

This invention is directed to the acylamino oxo or hydroxy substituted alkylamino thiazine and thiazepine compounds of formula I and salts thereof (I)

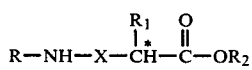

wherein

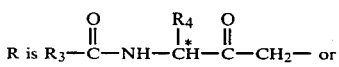

R is

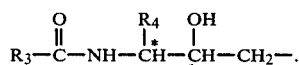

$R_3$ is

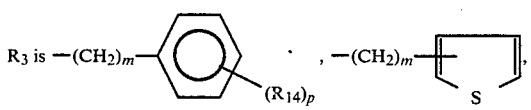

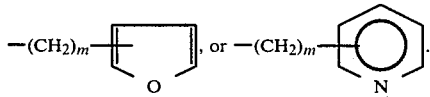

$R_4$ is hydrogen, lower akyl,

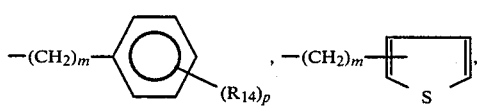

halo substituted lower alkyl, —(CH$_2$)$_m$-cycloalkyl,

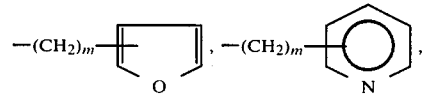

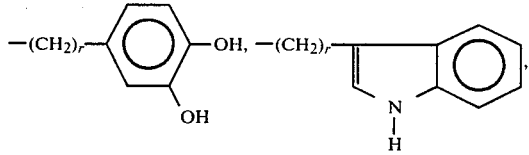

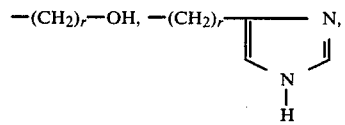

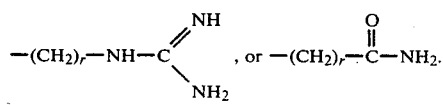

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if $R_{14}$ is hydrogen, methyl, methoxy, chloro, or fluoro.

r is one, two, three or four.

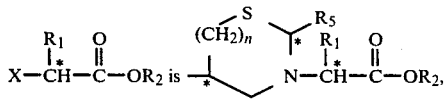

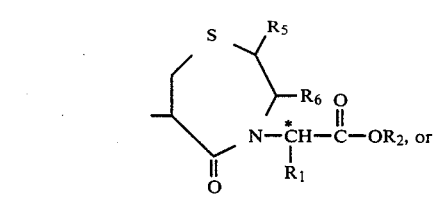

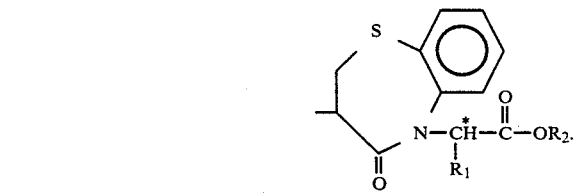

$R_1$ is hydrogen, lower alkyl, amino substituted lower alkyl, hydroxy substituted lower alkyl, or halo substituted lower alkyl.

n is one or two.

$R_5$ and $R_6$ are independently selected from hydrogen, lower alkyl, —(CH$_2$)$_m$-cycloalkyl and

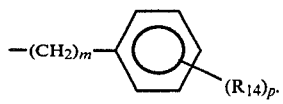

$R_2$ is hydrogen, lower alkyl, benzyl, benzhydryl, trimethylsilylethyl, salt forming ion,

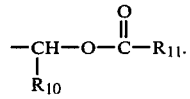

$R_{10}$ is hydrogen, lower alkyl, cycloalkyl or phenyl.
$R_{11}$ is hydrogen, lower alkyl, lower alkoxy, cycloalkyl, phenyl, benzyl, or phenethyl.

DETAILED DESCRIPTION OF THE INVENTION

This invention in its broadest aspects relates to the thiazine and thiazepine compounds of formula I above, to compositions containing such compounds and to the method of using such compounds as anti-hypertensive agents.

The term lower alkyl used in defining various symbols refers to straight or branched chain radicals having up to seven carbons. The preferred lower alkyl groups are up to four carbons with methyl and ethyl most preferred. Similarly, the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo, and fluoro.

The term halo substituted lower alkyl refers to such lower alkyl groups described above in which one or more hydrogens have been replaced by chloro, bromo, or fluoro groups such as trifluoromethyl, which is preferred, pentafluoroethyl, 2,2,2-trichloroethyl, chloromethyl, bromomethyl, etc. Similarly, the terms amino substituted lower alkyl and hydroxy substituted lower alkyl refer to such lower alkyl groups described above in which one or more hydrogens have been replaced by —NH₂ or—OH, i.e., aminomethyl, 2-aminoethyl, 3-hydroxypropyl, etc.

The symbols

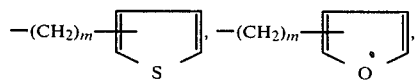

and 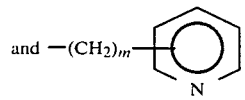

represent that the alkylene bridge is attached to an available carbon atom.

The acylamino oxo substituted alkylamino thiazines and thiazepines of formula I, i.e., R is

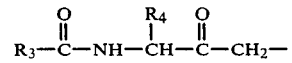

can be prepared as follows. A keto compound of the formula (II)

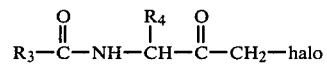

wherein halo is Cl or Br is reacted with the thiazine or thiazepine ester of the formula (III)

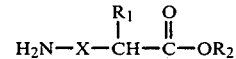

in the presence of base such as sodium bicarbonate. Removal of the $R_2$ ester group yields the acid products of formula I, i.e., $R_2$ is hydrogen.

The acylamino hydroxy substituted alkylamino substituted thiazines and thiazepines of formula I, i.e., R is

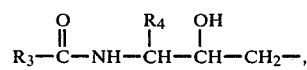

can be prepared by treating the corresponding oxo compound with a conventional reducing agent such as sodium borohydride, sodium cyanoborohydride, diisobutyl aluminum hydride, lithium tri t-butoxy aluminum hydride, etc.

The ester products of formula I wherein

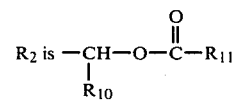

can be obtained by employing the thiazine or thiazepine of formula III in the above reaction with the ester group already in place.

The ester products of formula I wherein $R_2$

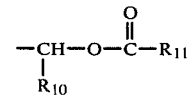

can also be obtained by treating the product of formula I wherein $R_2$ is hydrogen with a molar equivalent of the compound of the formula (IV)

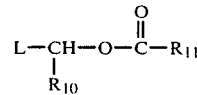

wherein L is a leaving group such as chlorine, bromine, tolylsulfonyloxy, etc.

The keto intermediate of formula II can be prepared by treating a keto compound of the formula (V)

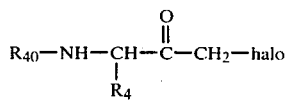

wherein R₄₀ is a protecting group such as benzyloxycarbonyl with hydrogen bromide and acetic acid followed by reaction with the acid halide of the formula (VI)

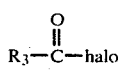

in the presence of base such as sodium bicarbonate.

The thiazine or thiazepine ester of formula III wherein R₅ is other than hydrogen can be prepared as follows. A phthaloyl amino acid of the formula (VII)

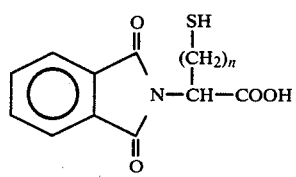

is reacted with an N-substituted glycine ester of the formula (VIII)

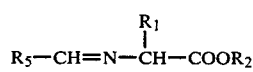

in the presence of a coupling agent such as dicyclohexylcarbodiimide to yield the N-protected thiazine or thiazepine of the formula (IX)

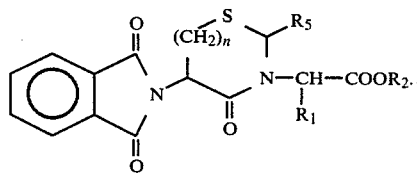

Treatment of the compound of formula IX with methylhydrazine removes the phthalimido protecting group and yields the desired thiazine or thiazepine ester of formula III.

The N-protected thiazine or thiazepine of formula IX can also be prepared by cyclizing sulfoxide of the formula (X)

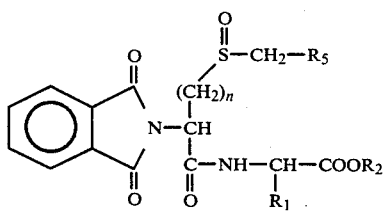

[prepared as set forth by Wolfe et al., Can. J. Chem., Vol. 57, p. 2412–2425 (1979)] by treatment with a mixture of trifluoroacetic acid anhydride and acetic anhydride followed by 2,6-lutidine.

The thiazine or thiazepine ester of formula III wherein R₅ is hydrogen can be prepared as follows. A dithiobis amino acid of the formula (XI)

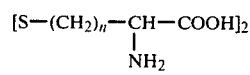

is reacted with N-carboethoxyphthalimide to give the compound of the formula (XII)

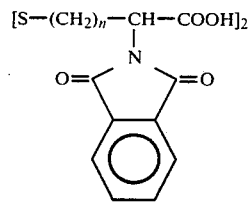

which is treated with a glycine ester hydrochloride in the presence of base and a coupling agent such as carbonyldiimidazole to yield the compound of the formula (XIII)

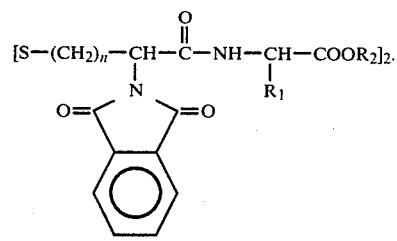

The dithiobis compound of formula XIII is treated with zinc dust to yield (XIV)

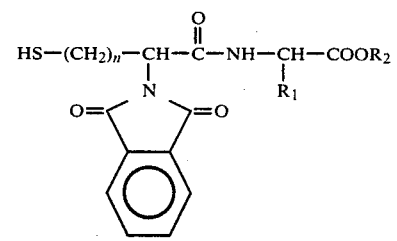

which is then treated with bromomethyl methyl ether in the presence of pyridine to give (XV)

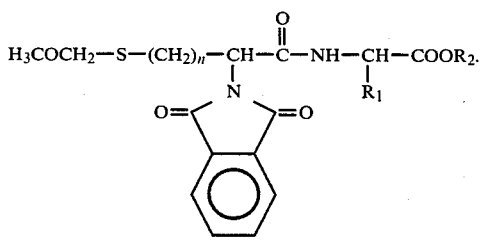

The compound of formula XV is cyclized by treatment with camphorsulfonic acid to give the N-protected thiazine or thiazepine of the formula (XVI)

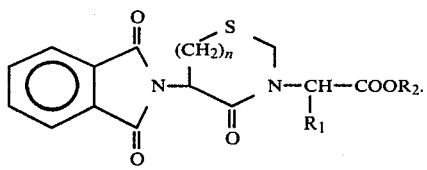

Treatment of the compound of formula XVI with methylhydrazine removes the phthalimido protecting group and yields the desired thiazine or thiazepine ester of formula III.

The thiazepine ester of formula III wherein X is

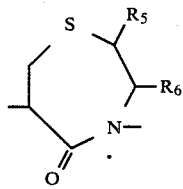

can be prepared as follows. An N-protected serine, for example, a t-butyloxycarbonyl N-protected serine, is treated with methyl iodide and cesium carbonate to yield the corresponding N-protected serine methyl ester. This methyl ester is then treated with diisopropylcarbodiimide and cuprous chloride to yield the N-protected dehydroalanine methyl ester of the formula (XVII)

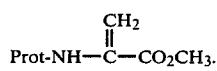

Treatment of the compound of formula XVII with the aminothiol hydrochloride of the formula (XVIII)

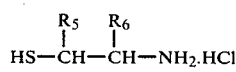

in the presence of base yields the methyl ester of the formula (XIX)

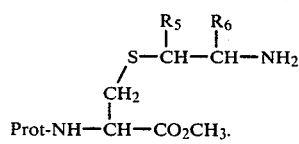

The compound of formula XIX is converted to the carboxylic acid and then cyclized by treatment with diphenylphosphoryl azide to yield the compound of the formula (XX)

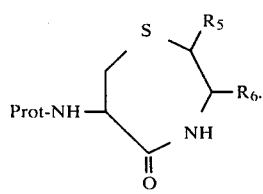

The thiazepine of formula XX is treated with a bromoacetate of the formula (XXI)

to yield the compound (XXII)

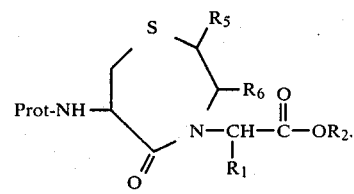

Removal of the protecting group, for example, by treating with hydrogen chloride in ethyl acetate when Prot is t-butyloxycarbonyl yields the desired thiazepine ester of formula III.

The thiazepine ester of formula III wherein X is

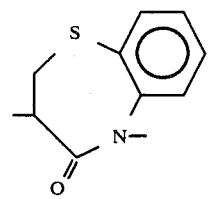

can be prepared as follows. The N-protected dehydroalanine methyl ester of formula XVII is reacted with 2-aminothiophenol and 2,6-lutidine to give the compound of formula (XXIII)

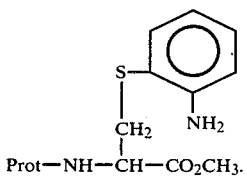

The methyl ester of formula XXIII is converted to the carboxylic acid and then cyclized by refluxing in xylene to give the compound of formula (XXIV)

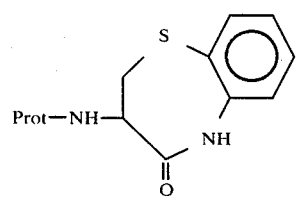

The thiazepine of formula XXIV is treated with the bromoacetate of formula XXI and the N-protecting group is removed as described above to give the desired thiazepine ester.

In the above reactions if $R_4$ is

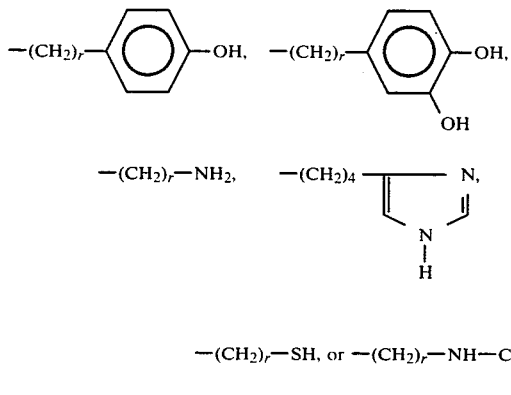

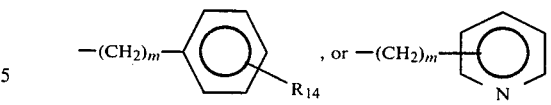

wherein m is zero, one, or two, $R_{14}$ is hydrogen, methyl, methoxy, methylthio, Cl, Br, F, or hydroxy, and r is an integer from 1 to 4, especially benzyl.

$R_5$ is hydrogen or phenyl, especially phenyl.

$R_2$ is hydrogen, alkali metal salt ion, or

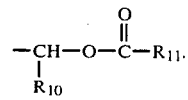

$R_{10}$ is hydrogen, straight or branched chain lower alkyl of 1 to 4 carbons, or cyclohexyl.

$R_{11}$ is straight or branched chain lower alkyl of 1 to 4 carbons.

or if $R_1$ is amino or hydroxy substituted lower alkyl then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Preferred compounds of this invention are those of formula I wherein:

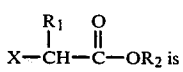

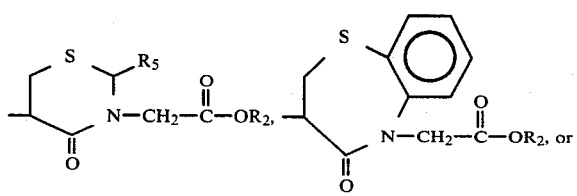

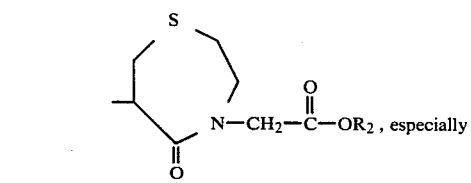

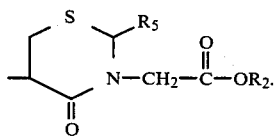

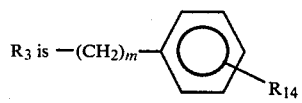

wherein m is zero, one or two and $R_{14}$ is hydrogen, methyl, methoxy, methylthio, Cl, Br, F, or hydroxy, especially phenyl.

$R_4$ is straight or branched chain lower alkyl of 1 to 4 carbons, $-(CH_2)_r-NH_2$, The compounds of this invention wherein $R_2$ is hydrogen form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, salts with amino acids like arginine, lysine and the like. The nontoxic, physiologically acceptable salts are preferred, although other salts are also useful, e.g., in isolating or purifying the product. The salts are formed using conventional techniques.

The symbol * is used to represent various asymmetric centers which may be present in the compounds of formula I. Thus, the compounds of this invention can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin or angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, mesolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade. AG-50W-X8 refers to a crosslinked polystyrene-divinylbenzene sulfonic acid cation exchange resin. HP-20 refers to a porous crosslinked polystyrene-divinylbenzene polymer resin.

EXAMPLE 1

[2S-[2α,5α(S)]]-5-[[3-(Benzoylamino)-2-oxo-4-phenylbutyl]amino]dihydro-4-oxo-2-phenyl-2H-1,3-thiazine-3(4H)-acetic acid, monohydrochloride (a) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperature for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°-179°.

(b) (S)-N-[3-Chloro-2-oxo-1-(phenylmethyl)propyl]-benzamide (S)-3-Amino-1-chloro-4-phenyl-2-butanone, hydrogen bromide (36.3 g., 130.3 mmole) is suspended in 520 ml. of dry tetrahydrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2-oxo-1-(phenylmethyl)propyl]benzamide; m.p. (160°) 170°-172° (dec.); $[\alpha]_D = -129°$ (c=1.7, dimethylformamide).

(c) N-Phthaloyl-L-cysteine

A solution of N,N'-diphthaloyl-L-cystine (19.5 g., 38.9 mmole) in a mixture of trifluoroacetic acid (60 ml.) and dry tetrahydrofuran (200 ml.) is cooled in an ice-bath under nitrogen and treated with zinc dust (15.3 g., 233.4 mmole) in three equal portions over a period of 15 minutes. The reaction is stirred cold for 2 hours, then filtered (celite) and concentrated in vacuo. The residue is partitioned between 600 ml. of ethyl acetate:ether (5:1) and a water-brine mixture. The organic layer is washed with water, brine and dried (MgSO$_4$). Removal of the solvents in vacuo yield 21.9 g. of crude product which is flash chromatographed on silica gel (400 g.) eluting with toluene:acetic acid (6:1). Fractions containing the desired product are combined to give 12.1 g. of N-phthaloyl-L-cysteine as an oil. $[\alpha]_D = -54.2°$ (c=1, methanol). TLC (toluene/acetic acid; 6:1) spot at $R_f = 0.30$.

(d) N-Benzylidineglycine, ethyl ester

A mixture of glycine, ethyl ester, hydrochloride (10 g., 71.6 mmole), triethylamine (14.5 g., 143.2 mmole) and anhydrous MgSO$_4$ (6.0 g., 50.1 mmole) in dry methylene chloride (150 ml.) is treated with a solution of benzaldehyde (7.6 g., 71.6 mmole) in methylene chloride (10 ml.) added over a period of 15 minutes. After 5 hours, the reaction mixture is filtered, concentrated in vacuo, and then partitioned between 400 ml. of ether and 50 ml. of water. The organic layer is washed with water and brine, dried (MgSO$_4$), and concentrated in vacuo to give 12.1 g. of N-benzylidineglycine, ethyl ester.

(e) (5R)-Dihydro-5-phthalimido-4-oxo-2-phenyl-2H-1,3-thiazine-3(4H)-acetic acid, ethyl ester (isomers A and B)

To a solution of N-phthaloyl-L-cysteine (15.8 g., 62.8 mmole) and N-benzylidineglycine, ethyl ester (12.3 g., 64.3 mmole) in dry chloroform (160 ml.) cooled in an ice bath under nitrogen is added dicyclohexylcarbodiimide (13.0 g., 62.8 mmole) in one portion. After 2 hours, the cold reaction mixture is filtered, concentrated in vacuo and redissolved in a mixture of ether (500 ml.) and chloroform (200 ml.). The organic extract is washed with saturated aqueous sodium bicarbonate, water, 5% potassium bisulfate and brine, dried (MgSO$_4$) and concentrated in vacuo to give 23.8 g. of crude product. Flash chromatography on silica (600 g.) eluting with hexane:ethyl acetate (3:1) yields 15.6 g. of (5R)-dihydro-5-phthalimido-4-oxo-2-phenyl-2H-1,3-thiazine-3(4H)-acetic acid, ethyl ester as a diastereomeric mixture.

This mixture is refluxed in 500 ml. of ether for 4 hours, then cooled in an ice-bath and filtered to yield 5.9 g. of (5R)-dihydro-5-phthalimido-4-oxo-2-phenyl-2H-1,3-thiazine-3(4H)-acetic acid, ethyl ester (isomer A); m.p. 166°-168°; $[\alpha]_D = -72.9°$ (c=1, chloroform). TLC (hexane/ethyl acetate; 1:1) spot at $R_f = 0.40$.

Anal. calc'd. for $C_{22}H_{20}N_2O_5S$: C, 62.25; H, 4.75; N, 6.60; S, 7.55 Found: C, 62.21; H, 4.82; N, 6.63; S, 7.52.

| | Col. I | Col. II | | Col. III | | |
|---|---|---|---|---|---|---|
| Example | $R_3$ | $R_4$ | n | $R_5$ | $R_1$ | $R_2$ |
| 3 | phenyl- | phenyl-$CH_2-$ | 2 | phenyl | $-CH_3$ | $-C_2H_4Si(CH_3)_3$ |
| 4 | $F$-phenyl-$CH_2-$ | phenyl-$CH_2-$ | 1 | $-H$ | $-H$ | $-C_2H_4Si(CH_3)_3$ |
| 5 | $H_3C$-phenyl- | phenyl-$(CH_2)_4-$ | 2 | $-H$ | $-H$ | $-C_2H_4Si(CH_3)_3$ |
| 6 | phenyl-$(CH_2)_2-$ | (2-thienyl)-$CH_2-$ | 1 | $-CH_3$ | $-H$ | $-C_2H_4Si(CH_3)_3$ |
| 7 | phenyl- | (3-pyridyl)-$CH_2-$ | 2 | $-H$ | $-H$ | $-C_2H_4Si(CH_3)_3$ |
| 8 | phenyl- | $H_3CO$-phenyl-$CH_2-$ | 1 | phenyl | $-CF_3$ | $-C_2H_4Si(CH_3)_3$ |
| 9 | phenyl- | (indol-3-yl)-$CH_2-$ | 2 | phenyl | $-H$ | $-C_2H_4Si(CH_3)_3$ |
| 10 | phenyl- | phenyl-$H_2COCHN(H_2C)_4-$ | 1 | cyclohexyl | $-H$ | $-C_2H_4Si(CH_3)_3$ |
| 11 | (2-thienyl)-$CH_2-$ | $H_3C-$ | 2 | $-H$ | $-H$ | $-C_2H_4Si(CH_3)_3$ |
| 12 | (2-furyl)- | phenyl-$CH_2-$ | 1 | $-CH_2$-phenyl | $-H$ | $-C_2H_4Si(CH_3)_3$ |
| 13 | (4-pyridyl)- | phenyl-$CH_2-$ | 2 | $-C(CH_3)_3$ | $-H$ | $-C_2H_4Si(CH_3)_3$ |
| 14 | phenyl- | $F_3C-$ | 1 | $-H$ | $-H$ | $-C_2H_4Si(CH_3)_3$ |
| 15 | phenyl- | (3-furyl)-$CH_2-$ | 2 | $-H$ | $-C_2H_5$ | $-C_2H_4Si(CH_3)_3$ |
| 16 | phenyl- | (3-pyridyl)-$CH_2-$ | 1 | phenyl | $-H$ | $-C_2H_4Si(CH_3)_3$ |

Trituration of the remainder of the diastereomeric product mixture with 125 ml. of refluxing ether affords a second batch of isomer A (0.9 g., m.p. 162°–164°). The residue is triturated with ether to give 0.75 g. of insoluble substance (presumably largely isomer A) and 7.1 g. of material enriched in isomer B. The enriched isomer B (6.0 g.) is chromatographed on two connected Waters Prep LC columns eluted with hexane:ethyl acetate (3:1). Pooling of the product containing fractions yields 4.8 g. of purified (5R)-dihydro-5-phthalimido-4-oxo-2-phenyl-2H-1,3-thiazine-3(4H)-acetic acid, ethyl ester (isomer B); m.p. 66°–68°; $[\alpha]_D = -101.2°$ (c=1, chloroform). TLC same as isomer A.

Anal. calc'd. for $C_{22}H_{20}N_2O_5S \cdot 0.2H_2O$: C, 61.83; H, 4.79; N, 6.55; S, 7.50 Found: C, 61.83; H, 5.07; N, 6.25; S, 7.42.

(f)
(5R)-Dihydro-5-Phthalimido-4-oxo-2-phenyl-2H-1,3-thiazine-3(4H)-acetic acid, 2-(trimethylsilyl)ethyl ester (isomer B)

A mixture of (5R)-dihydro-5-phthalimido-4-oxo-2-phenyl-2H-1,3-thiazine-3(4H)-acetic acid, ethyl ester (isomer B) (2.5 g., 5.9 mmole), 2-trimethylsilylethanol (14.0 g., 118 mmole), and titanium (IV) ethoxide (338 mg., 1.48 mmole) is heated at 100° under nitrogen for 5 hours and then cooled to room temperature. The reaction mixture is then diluted with 200 ml. of ether and stirred with 25 ml. of 1N hydrochloric acid for 10 minutes. Next, the organic solution is separated, rinsed with water, saturated sodium bicarbonate, water, and brine, dried ($MgSO_4$), and concentrated in vacuo. Most of the excess 2-trimethylsilylethanol is removed by distillation using a 40° oil bath and an ice-cooled receiving flask. After further pumping in vacuo, the residue (3.2 g.) is flash chromatographed on 160 g. of LPS-1 silica gel eluted with hexane:ethyl acetate (5:1) to give 2.2 g. of (5R)-dihydro-5-phthalimido-4-oxo-2-phenyl-2H-1,3-thiazine-3(4H)-acetic acid, 2-(trimethylsilyl)ethyl ester (isomer B); m.p. 65°–66°; $[\alpha]_D = -75.0°$ (c=1, chloroform). TLC (hexane:ethyl acetate; 2:1) spot at $R_f = 0.46$.

Anal. calc'd. for $C_{25}H_{28}N_2O_5SSi$: C, 60.46; H, 5.68; N, 5.64; S, 6.46 Found: C, 60.44; H, 5.69; N, 5.50; S, 6.43.

(g)
(5R)-Dihydro-5-amino-4-oxo-2-phenyl-2H-1,3-thiazine-3(4H)-acetic acid, 2-(trimethylsilyl)ethyl ester (isomer B)

A solution of (5R)-dihydro-5-phthalimido-4-oxo-2-phenyl-2H-1,3-thiazine-3(4H)-acetic acid, 2-(trimethylsilyl)ethyl ester (isomer B) (2.01 g., 4.05 mmole) in dry chloroform (9 ml.) under nitrogen at room temperature is treated with methylhydrazine (317 mg., 6.88 mmole). After 12 hours, an additional 0.1 ml. of methylhydrazine is added and the reaction is stoppered and stirred overnight. The reaction mixture is then diluted with an additional 100 ml. of ether and the solution is rinsed with 25 ml. portions of saturated sodium bicarbonate, water, and brine, dried ($MgSO_4$), and concentrated in vacuo to give 1.55 g. of crude (5R)-dihydro-5-amino-4-oxo-2-phenyl-2H-1,3-thiazine-3(4H)-acetic acid, 2-(trimethylsilyl)ethyl ester (isomer B); $[\alpha]_D = -47.3°$ (c=1, chloroform).

(h)
[2S-[2α,5α(S)]]-5-[[3-(Benzoylamino)-2-oxo-4-phenylbutyl]amino]dihydro-4-oxo-2-phenyl-2H-1,3-thiazine-3(4H)-acetic acid, monohydrochloride A mixture of (5R)-dihydro-5-amino-4-oxo-2-phenyl-2H-1,3-thiazine-3(4H)-acetic acid, 2-(trimethylsilyl)ethyl ester (1.6 g., 4.5 mmole), (S)-N-[3-chloro-2-oxo-1-(phenylmethyl)propyl]benzamide (1.2 g., 4.0 mmole), sodium bicarbonate (336 mg., 4.0 mmole), and sodium iodide (600 mg., 4.0 mmole) in dimethylformamide (20 ml.) is stirred under nitrogen at 25° for 17 hours. The reaction mixture is then poured into 10% aqueous sodium bicarbonate solution and extracted with ether. The extract is washed with 1N hydrochloric acid solution, dried ($MgSO_4$), and concentrated to give a red oil (2.0 g.).

This crude oil is dissolved in 1.4N hydrochloric acid in acetic acid solution (25 ml.) and is stirred at 25° for 2.5 hours. The mixture is concentrated in vacuo to give a reddish solid. This material is chromatographed on HP-20 using an elution gradient [0.01N aqueous hydrochloric acid:methanol, 40:60 to 10:90]. Fractions containing the major product (TLC) are combined and concentrated. The residue is triturated with methanol/ether to give 350 mg. of [2S-[2α,5α(S)]]-5-[[3-(benzoylamino)-2-oxo-4-phenylbutyl]amino]-dihydro-4-oxo-2-phenyl-2H-1,3-thiazine-3(4H)-acetic acid, monohydrochloride; m.p. dec. greater than 110°; $[\alpha] = -82°$ (c=1.0, methanol). TLC (silica gel; chloroform:methanol:acetic acid, 10:1:1) $R_f = 0.56$. IR: (KBr) (1648, 1731 $cm^{-1}$).

Anal. calc'd. for $C_{29}H_{29}N_3O_5S \cdot HCl \cdot 1.37 H_2O$: C, 58.76; H, 5.57; N, 7.09; S, 5.41; Cl, 5.98 Found: C, 58.76; H, 5.34; N, 7.04; S, 5.56; Cl, 6.24.

EXAMPLE 2

[2S-[2α,5α(S)]]-5-[[3-(Benzoylamino)-2-hydroxy-4-phenylbutyl]amino]dihydro-4-oxo-2-phenyl-2H-1,3-thiazine-3(4H)-acetic acid The product from Example 1 is dissolved in tetrahydrofuran and water and while at 0° sodium borohydride is added. After stirring for several hours at 0°, the reaction is quenched with 1N hydrochloric acid and extracted with ethyl acetate. The organic fraction is washed with 1N hydrochloric acid, 1N sodium bicarbonate, and brine, dried ($MgSO_4$), and the solvent is removed at reduced pressure to give [2S-[2α,5α(S)]]-5-[[3-(benzoylamino)-2-hydroxy-4-phenylbutyl]amino]-dihydro-4-oxo-2-phenyl-2H-1,3-thiazine-3(4H)-acetic acid as a diastereomeric mixture.

EXAMPLES 3–28

Following the procedure of Example 1 but employing the keto compound shown in Col. I and the thiazine shown in Col. II, one obtains the product shown in Col. III. The $R_4$ protecting groups shown in Examples 10, 18, 19, 20 and 21 are removed as the last step of the synthesis.

-continued

| | | | | | | |
|---|---|---|---|---|---|---|
| 17 |  | 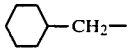CH₂— | 2 | —C₂H₅ | —H | —C₂H₄Si(CH₃)₃ |
| 18 |  | 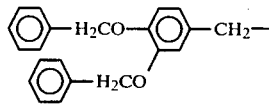 | 1 |  | —H | —C₂H₄Si(CH₃)₃ |
| 19 |  | 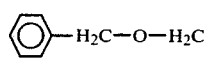—H₂C—O—H₂C | 1 | —H | —H | —C₂H₄Si(CH₃)₃ |
| 20 |  | 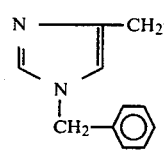 | 2 | —H | —H | —C₂H₄Si(CH₃)₃ |
| 21 |  | 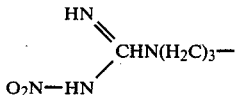 | 1 |  | —H | —C₂H₄Si(CH₃)₃ |
| 22 |  | H₃C—S—H₂C— | 1 | 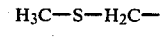 | —H | —C₂H₄Si(CH₃)₃ |
| 23 |  | H₅C₂— | 2 | —H | —H | —C₂H₄Si(CH₃)₃ |
| 24 |  | —(CH₂)₃— | 1 | —H | —CH₃ | —C₂H₄Si(CH₃)₃ |
| 25 |  | 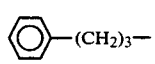—CH₂— | 1 |  | —H | 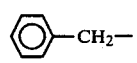 |
| 26 |  | —CH₂— | 2 |  | —H |  |
| 27 | 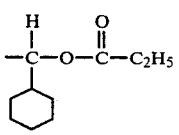 | —CH₂— | 1 |  | —H |  |
| 28 | 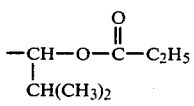 | —CH₂— | 1 | —CH₃ | —H | 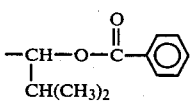 |

The keto products of Examples 3 to 28 can be treated with a reducing agent such as sodium borohydride according to the procedure of Example 2 to give the corresponding hydroxy products.

EXAMPLE 29

Tetrahydro-6-[[3-(Benzoylamino)-2-oxo-4-phenylbutyl-]amino]-5-oxo-1,4-thiazepine-4(5H)-acetic acid, monolithium salt (a) N-[(1,1-Dimethylethoxy)carbonyl]-L-serine, methyl ester To a solution of N-[(1,1-dimethylethoxy)carbonyl]-L-serine (20.5 g., 0.1 mole), methanol (50 ml.), and water (10 ml.) is added cesium carbonate (16.3 g., 0.5 eq.). After 5 minutes the solution becomes homogeneous, the methanol is stripped, and the residual water is removed azeotropically with acetonitrile (three times). The resulting foam is taken up in dry dimethylformamide (250 ml.) and treated with methyl iodide (6.2 ml., 10 eq.) at 25° under argon (slight exotherm). After 25 hours the reaction mixture is taken up in ethyl acetate and washed successively with saturated sodium bicarbonate, 5% potassium bisulfate, brine, dried (MgSO₄), and evaporated to give 17.5 g. of N-[(1,1-dimethylethoxy)-carbonyl]-L-serine, methyl ester as a light green oil. TLC (ethyl acetate) single spot at $R_f$=0.71.

(b) 2-[[(1,1-Dimethylethoxy)carbonyl]amino]-2-propenoic acid, methyl ester

A mixture of N-[(1,1-dimethylethoxycarbonyl]-L-serine, methyl ester (18.4 g., 83.9 mmole), diisopropylcarbodiimide (14.4 ml., 1.1 eq.) and acetonitrile (30 ml.) is treated with cuprous chloride (2.6 g., 0.3 eq.) at 25° in an argon atmosphere. After stirring the green mixture for 16 hours, ethyl acetate is added and the resulting mixture is filtered (celite bed) and evaporated. The gelatinous residue (19.0 g.) is filtered through a pad of silica (100 g.) eluting with ethyl acetate/hexane (1:16) to give 8.2 g. of 2-[[(1,1-dimethylethoxy)carbonyl]amino]-2-propenoic acid, methyl ester as a light green liquid. TLC (ethyl acetate/hexane; 1:16) major spot at $R_f = 0.29$.

(c) S-(2-Aminoethyl)-N-[(1,1-dimethylethoxy)carbonyl]-L-cysteine, methyl ester A mixture of 2-aminoethanethiol, hydrochloride (5.5 g., 1.2 eq.), triethylamine (16.6 ml., 2.4 eq.), and methylene chloride (20 ml.) at 0° (ice bath) under argon is treated dropwise with 2-[[(1,1-dimethylethoxy)carbonyl]amino]-2-propenoic acid, methyl ester (8.2 g., 40.8 mmole) in methylene chloride (30 ml.) over a 15 minute period. The ice bath is then removed and the resulting solution is stirred for 20 hours. The reaction mixture is taken up in ethyl acetate, filtered, and washed successively with water (twice), saturated sodium bicarbonate, brine, and evaporated. The gelatinous residue (9.4 g.) is taken up in ether and added dropwise to a solution of oxalic acid (3.6 g.)/ethyl ether (250 ml.) to obtain the oxalate salt as a white solid after filtration. The oxalate salt is taken up in water and basified with saturated sodium bicarbonate. The resulting oil is extracted into methylene chloride (approximately 20 times) to give 7.5 g. of S-(2-aminoethyl)-N-[(1,1-dimethylethoxy)carbonyl]-L-cysteine, methyl ester as an oil after evaporation. TLC (methylene chloride/methanol/acetic acid; 8:1:1) major spot at $R_f = 0.52$.

(d) (Hexahydro-5-oxo-1,4-thiazepin-6-yl)carbamic acid, (1,1-dimethylethyl)ester A mixture of S-(2-aminoethyl)-N-[(1,1-dimethylethoxy)carbonyl]-L-cysteine, methyl ester (7.5 g., 26.9 mmole), 1N sodium hydroxide (31.0 ml., 1.15 eq.), and dioxane (30 ml.) is stirred at room temperature for 2 hours. The reaction is then treated with 1N hydrochloric acid (4.1 ml.) to quench excess hydroxide. The dioxane and water are evaporated and the residual water is removed azeotropically with acetonitrile (twice). The resulting foam is taken into dry dimethylformamide (100 ml.), treated with diphenylphosphoryl azide (6.5 ml., 1.1 eq.), and stirred under argon at 25° for 3.5 days. The reaction mixture is diluted with ethyl acetate and washed successively with water, saturated sodium bicarbonate, 5% potassium bisulfate, brine, dried (MgSO$_4$), and evaporated. The residue (3.0 g.) is taken up in hot ethyl acetate and upon cooling 1.1 g. of the product crystallizes as a colorless solid. The mother liquor (1.9 g.) is chromatographed on silica (70 g.) eluting with 5% acetone/methylene chloride to give an additional 0.4 g. of product as a slightly colored solid. A small portion of the product is recrystallized from toluene to give (hexahydro-5-oxo-1,4-thiazepin-6-yl)carbamic acid, (1,1-dimethylethyl)ester as fine colorless needles; m.p. 199.5°–201°. TLC (10% acetone/methylene chloride) single spot at $R_f = 0.49$.

Anal. calc'd. for $C_{10}H_{18}N_2O_3S$: C, 48.76; H, 7.36; N, 11.37; S, 13.02 Found: C, 48.56; H, 7.09; N, 11.35; S, 13.01.

(e) 6-[[(1,1-Dimethylethoxy)carbonyl]amino]tetrahydro-5-oxo-1,4-thiazepine-(5H)-acetic acid, ethyl ester A suspension of (hexahydro-5-oxo-1,4-thiazepin-6-yl)carbamic acid, (1,1-dimethylethyl)ester (1.35 g., 5.48 mmole) in dry tetrahydrofuran (10 ml.) under argon at 0° (ice bath) is treated with potassium tert-butoxide (0.68 g., 1.1 eq.) to effect an orange homogeneous solution. After 5 minutes, ethyl bromoacetate (1.1 ml., 1.8 eq.) is added, the ice bath removed, and the reaction mixture is stirred for 2 hours. The reaction mixture is then diluted with ethyl acetate and washed successively with saturated sodium bicarbonate, 5% potassium bisulfate, brine, dried (MgSO$_4$) and evaporated. The residue is chromatographed on silica (85 g.) eluting with 5% acetone/methylene chloride to give 1.65 g. of 6-[[(1,1-dimethylethoxy)carbonyl]amino]tetrahydro-5-oxo-1,4-thiazepine-4(5H)-acetic acid, ethyl ester as an oil following evaporation. TLC (10% acetone/methylene chloride) single spot at $R_f = 0.71$.

(f) 6-Amino-tetrahydro-5-oxo-1,4-thiazepine-4(5H)-acetic acid, ethyl ester, hydrochloride A mixture of 6-[[(1,1-dimethylethoxy)carbonyl]amino]-tetrahydro-5-oxo-1,4-thiazepine-4(5H)-acetic acid, ethyl ester (1.65 g., 4.96 mmole) and ethyl acetate (10 ml.) at 0° (ice bath) is treated with cold saturated hydrochloric acid/ethyl acetate (20 ml.). After stirring for 2 hours at 0°, nitrogen is passed through the solution to remove excess hydrochloric acid. The ethyl acetate is evaporated and the residue is triturated with ether (three times) to give 1.35 g. of 6-amino-tetrahydro-5-oxo-1,4-thiazepine-4(5H)-acetic acid, ethyl ester, hydrochloride as a yellow solid. TLC (methylene chloride/methanol/acetic acid; 8:1:1) single spot at $R_f = 0.5$ (visualized with ninhydrin and heat).

Anal. calc'd for $C_9H_{16}N_2O_3S \cdot HCl \cdot 0.5H_2O$: C, 38.98; H, 6.52; N, 10.10; S, 11.56; Cl, 12.78 Found: C, 38.98; H, 6.73; N, 9.66; S, 11.32; Cl, 12.80.

(g) Tetrahydro-6-[[3-(Benzoylamino)-2-oxo-4-phenylbutyl]amino]-5-oxo-1,4-thiazepine-4(5H)-acetic acid, ethyl ester 6-Amino-tetrahydro-5-oxo-1,4-thiazepine-4(5H)-acetic acid, ethyl ester, hydrochloride is reacted with (S)-N-[3-chloro-2-oxo-1-(phenylmethyl)propyl]benzamide according to the procedure of Example 1(h) to give tetrahydro-6-[[3-(benzoylamino)-2-oxo-4-phenylbutyl]amino]-5-oxo-1,4-thiazepine-4(5H)-acetic acid, ethyl ester.

(h) Tetrahydro-6-[[3-(Benzoylamino)-2-oxo-4-phenylbutyl]amino]-5-oxo-1,4-thiazepine-4(5H)-acetic acid, monolithium salt A mixture of the ester product from part (g), is treated with dry acetonitrile and 1N sodium hydroxide. After several hours, the acetonitrile is evaporated and the product is obtained chromatographically. The product containing fractions are combined and applied to an AG 50 W×8(Li+) column eluting with water. The desired fractions are combined, filtered, and lyophilized to give tetrahydro-6-[[3-(benzoylamino)-2-oxo-4-phenylbutyl]amino]-5-oxo-1,4-thiazepine-4(5H)-acetic acid, monolithium salt.

EXAMPLE 30

Tetrahydro-6-[[3-(Benzoylamino)-2-hydroxy-4-phenylbutyl]amino]-5-oxo-1,4-thiazepine-4(5H)-acetic acid The product from Example 29 is dissolved in tetrahydrofuran and water and while at 0° sodium borohydride is added. After stirring for several hours at 0°, the reaction is quenched with 1N hydrochloric acid and extracted with ethyl acetate. The organic fraction is washed with 1N hydrochloric acid, 1N sodium bicarbonate, and brine, dried (MgSO$_4$), and the solvent is removed at reduced pressure to give tetrahydro-6-[[3-(benzoylamino)-2-hydroxy-4-phenylbutyl]amino]-5-oxo-1,4-thiazepine-4(5H)-acetic acid.

EXAMPLES 31–40

Following the procedure of Example 29 but employing substituted 2-aminoethanethiol shown below in Col. I in part (c) one obtains the thiazepine shown below in Col. II. This thiazepine is then reacted with the keto compound shown in Col. III to give the ester product shown in Col. IV. The R$_2$ ester group can be removed to give the corresponding acid which can then be converted to a salt.

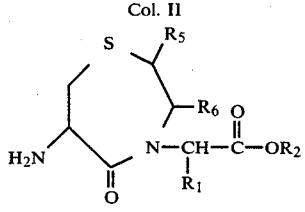

| Example | R$_5$ | R$_6$ | R$_1$ | R$_2$ | R$_3$ | R$_4$ |
|---|---|---|---|---|---|---|
| 31 | —CH$_3$ | —H | —H | —C$_2$H$_5$ | 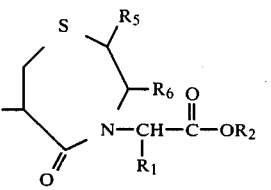 | 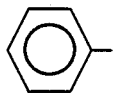 |
| 32 | —H | —CH$_3$ | —H | —C$_2$H$_5$ | 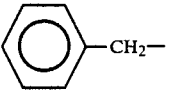 | 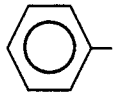 |
| 33 | —H | —H | —CH$_3$ | —C$_2$H$_5$ | 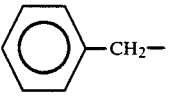 | 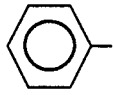 |
| 34 | 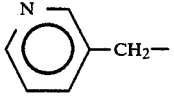 | —H | —H | —C$_2$H$_5$ | 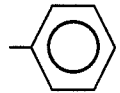 | 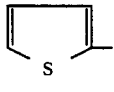 |
| 35 | —H | 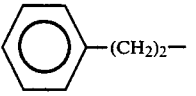 | —H | —C$_2$H$_5$ | 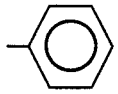 | 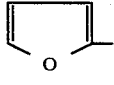 |
| 36 | —CH$_3$ | —CH$_3$ | —H | —C$_2$H$_5$ | 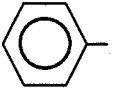 | 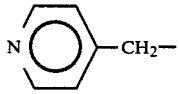 |

-continued

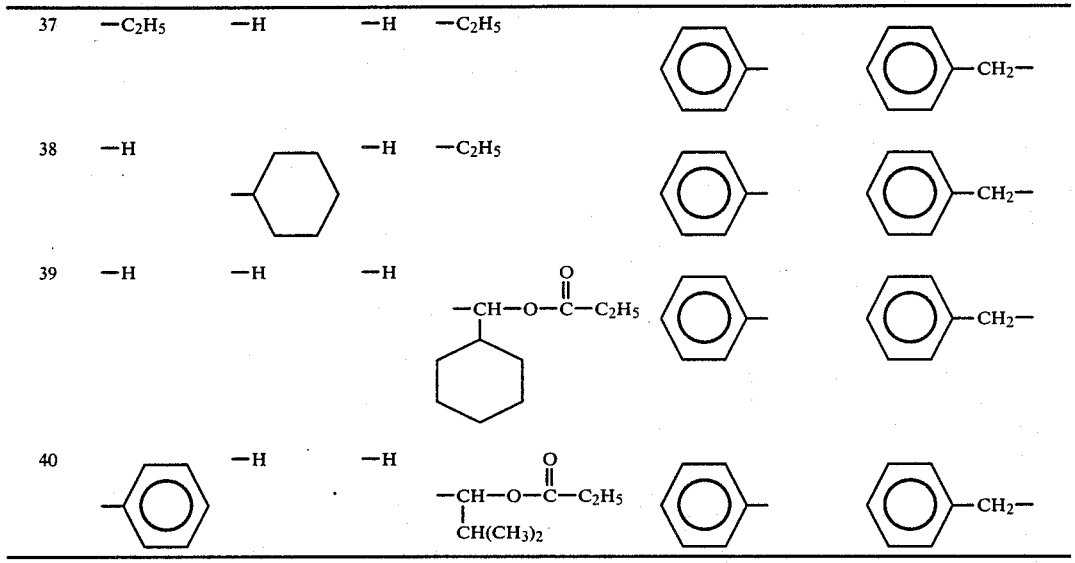

The keto products of Examples 31 to 40 can be treated with a reducing agent such as sodium borohydride according to the procedure of Example 2 to give the corresponding hydroxy products.

EXAMPLE 1

(±)-Dihydro-3-[[3-(Benzoylamino)-2-oxo-4-phenylbutyl]amino]-4-oxo-1,5-benzothiazepin-5(2H)-acetic acid

(a)
S-(2-Aminophenyl)-N-[(1,1-dimethylethoxy)carbonyl]-L-cysteine, methyl ester To a mixture of 2-amino-thiophenol (1.9 g., 15.4 mmole), methylene chloride (15 ml.), and 2,6-lutidine (1.8 ml., 1.0 eq.) at −20° (chloroform dry ice) is added 2-[[(1,1-dimethylethoxy)carbonyl]amino]-2-propenoic acid, methyl ester (3.0 g., 1.0 eq.) dropwise over 5 minutes. After one hour the cooling bath is removed and the reaction mixture is stirred for an additional 16 hours. The reaction mixture is diluted with ethyl acetate and washed with saturated sodium bicarbonate, water, brine, dried (MgSO$_4$), and evaporated. The residue (4.1 g.) is chromatographed on silica (125 g.) eluting with hexane/ethyl acetate (5:1) to give 2.5 g. of S-(2-aminophenyl)-N-[(1,1-dimethylethoxy)carbonyl]-L-cysteine, methyl ester as an oil after evaporation.

(b)
S-(2-Aminophenyl)-N-[(1,1-dimethylethoxy)carbonyl]-L-cysteine

A mixture of S-(2-aminophenyl)-N-[(1,1-dimethylethoxy)carbonyl]-L-cysteine, methyl ester (1.0 g., 3.1 mmole), 1N sodium hydroxide (3.1 ml., 1.0 eq.), and dioxane (6 ml.) is stirred at room temperature in an argon atmosphere for one hour. The reaction mixture is washed with ethyl acetate, neutralized with 1N hydrochloric acid (3.1 ml.) and extracted with methylene chloride (twice). The combined extracts are dried (MgSO$_4$) and evaporated to give 1.0 g. of S-(2-aminophenyl)-N-[(1,1-dimethylethoxy)carbonyl]-L-cysteine as a foam. TLC (methylene chloride/acetic acid/methanol; 100:5:5) major spot at R$_f$=0.5. The product crystallizes from xylene to give S-(2-aminophenyl)-N-[(1,1-dimethylethoxy)carbonyl]-L-cysteine as a fluffy crystalline solid; m.p. 109°–111°.

Anal. calc'd. for C$_{14}$H$_{20}$N$_2$O$_4$S: C, 53.83; H, 6.45; N, 8.97; S, 10.26 Found: C, 53.51; H, 6.28; N, 8.99; S, 10.26.

(c)
(±)-(2,3,4,5-Tetrahydro-4-oxo-1,5-benzothiazepin-3-yl)carbamic acid, 1,1-dimethylethyl ester A suspension of S-(2-aminophenyl)-N-[(1,1-dimethylethoxy)carbonyl]-L-cysteine (0.65 g., 2.1 mmole) in xylene (15 ml.) is refluxed in a flask equipped with a Dean-Stark trap for 7 hours. Upon cooling of the reaction mixture the product crystallizes. The solid is collected by filtration, washed with xylene, and dried (high vacuum) to give 0.4 g. of (±)-(2,3,4,5-tetrahydro-4-oxo-1,5-benzothiazepin-3-yl)carbamic acid, 1,1-dimethylethyl ester as an off-white crystalline solid; m.p. 197°–200° (decomp.).

Anal. calc'd. for C$_{14}$H$_{18}$N$_2$O$_3$S: C, 57.12; H, 6.16; N, 9.52; S, 10.89 Found: C, 56.88; H, 6.17; N, 9.40; S, 10.87.

(d)
(±)-3-[[(1,1-Dimethylethoxy)carbonyl]amino]-3,4-dihydro-4-oxo-1,5-benzothiazepine-5(2H)-acetic acid, ethyl ester A mixture of (±)-(2,3,4,5-tetrahydro-4-oxo-1,5-benzothiazepin-3-yl)carbamic acid, 1,1-dimethylethyl ester (0.8 g., 2.7 mmole), tetrahydrofuran (10 ml.) and potassium tert-butoxide (0.4 g., 1.3 eq.) is stirred at 0° (ice bath) under argon for 10 minutes and then treated with ethyl bromoacetate (0.5 g., 1.7 eq.). After 3 minutes the ice bath is removed and the mixture is stirred for one hour. The reaction mixture is then diluted with ethyl acetate and washed successively with saturated sodium bicarbonate, 5% potassium bisulfate, and brine, dried (MgSO$_4$) and evaporated. The residue (1.3 g.) is chromatographed on silica (60 g.) eluting with hexane/ethyl acetate (4:1) to give 1.0 g. of (±)-3-[[(1,1-dimethylethoxy)carbonyl]amino]-3,4-dihydro-4-oxo-1,5-benzothiazepine-5(2H)-acetic acid, ethyl ester as a foam. TLC (hexane/ethyl acetate; 4:1) single spot at R$_f$=0.21.

(e)
(±)-3-Amino-3,4-dihydro-4-oxo-1,5-benzothiazepine-5(2H)-acetic acid, ethyl ester A mixture of (±)-3-[[(1,1-dimethylethoxy)carbonyl]amino]-3,4-dihydro-4-oxo-1,5-benzothiazepine-5(2H)-acetic acid, ethyl ester (1.0 g., 2.6 mmole), methylene chloride (5 ml.), and trifluoroacetic acid (3 ml.) is stirred under argon at 25° for 30 minutes. The methylene chloride and trifluoroacetic acid are removed in vacuo and the residue is taken up in ethyl acetate and the hydrochloride salt is precipitated with saturated hydrochloric acid/ethyl ether. The white solid is collected by filtration and washed with 2:1 ethyl acetate/ethyl ether to yield 0.7 g. of (±)-3-amino-3,4-dihydro-4-oxo-1,5-benzothiazepine-5(2H)-acetic acid, ethyl ester as a white solid; m.p. 231°-233° (decomp.). TLC (methylene chloride/acetic acid/methanol; 100:5:5) single spot at $R_f=0.08$.

Anal. calc'd. for $C_{13}H_{16}N_2O_3S \cdot HCl$: C, 49.29; H, 5.41; N, 8.84; S, 10.12; Cl, 11.37 Found: C, 48.87; H, 5.31; N, 8.80; S, 10.05; Cl, 11.37.

(f)
(±)-Dihydro-3-[[3-(Benzoylamino)-2-oxo-4-phenylbutyl]amino]-4-oxo-1,5-benzothiazepine-5(2H)-acetic acid, ethyl ester (±)-3-Amino-3,4-dihydro-4-oxo-1,5-benzothiazepine-5(2H)-acetic acid, ethyl ester is reacted with (S)-N-[3-chloro-2-oxo-1-(phenylmethyl)propyl]benzamide according to the procedure of Example 1(h) to yield (±)-dihydro-3-[[3-benzoylamino)-2-oxo-4-phenylbutyl]amino]-4-oxo-1,5-benzothiazepine-5(2H)-acetic acid, ethyl ester.

(g)
(±)-Dihydro-3-[[3-(Benzoylamino)-2-oxo-4-phenylbutyl]amino]-4-oxo-1,5-benzothiazepine-5(2H)-acetic acid The ester product from part (f) is treated with 1N sodium hydroxide according to the procedure of Example 29(h) to yield (±)-dihydro-3-[[3-(benzoylamino)-2-oxo-4-phenylbutyl]amino]-4-oxo-1,5-benzothiazepine-5(2H)-acetic acid.

Substitution of the various keto compounds shown in Col. I of Examples 3 to 28 for the (S)-N-[3-chloro-2-oxo-1-(phenylmethyl)propyl]benzamide in part (f) yields other compounds within the scope of this invention.

EXAMPLE 42
(±)-Dihydro-3-[[3-(Benzoylamino)-2-hydroxy-4-phenylbutyl]amino]-4-oxo-1,5-benzothiazepine-5(2H)-acetic acid Treatment of the product of Example 41 with sodium borohydride according to the procedure of Example 2 yields (±)-dihydro-3-[[3-(benzoylamino)-2-hydroxy-4-phenylbutyl]amino]-4-oxo-1,5-benzothiazepine-5(2H)-acetic acid.

EXAMPLE 43

1000 tablets each containing the following ingredients:

| | |
|---|---|
| [2S—[2α,5α(S)]]-5-[[3-(Benzoyl-amino)-2-oxo-4-phenylbutyl]-amino]dihydro-4-oxo-2-phenyl-2H—1,3-thiazine-3(4H)—acetic acid, monohydrochloride | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing the [2S-[2α,5α(S)]]-5[[3-(benzoylamino)-2-oxo-4-phenylbutyl]amino]dihydro-4-oxo-2-phenyl-1,3-thiazine-3(4H)-acetic acid, monohydrochloride and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 42 can be prepared as can tablets containing 50 mg. of active ingredient.

EXAMPLE 44

Two piece #1 gelatin capsules each containing 100 mg. of [2S-[2α,5α(S)]]-5-[[3-(benzoylamino)-2-hydroxy-4-phenylbutyl]amino]dihydro-4-oxo-2-phenyl-2H-1,3-thiazine-3(4H)-acetic acid are filled with a mixture of the following ingredients:

| | |
|---|---|
| [2S—[2α,5α(S)]]-5-[[3-(benzoyl-amino)-2-hydroxy-4-phenylbutyl]-amino]dihydro-4-oxo-2-phenyl-2H—1,3-thiazine-3(4H)—acetic acid | 100 mg. |
| Magnesium stearate | 7 mg. |
| Lactose | 193 mg. |
| | 300 mg. |

In a similar manner, capsules containing 100 mg of the product of any of Examples 1 and 3 to 42 can be prepared.

EXAMPLE 45

An injectable solution is prepared as follows:

| | |
|---|---|
| (±)-Dihydro-3-[[3-(Benzoyl-amino)-2-oxo-4-phenylbutyl]-amino]-4-oxo-1,5-benzothia-zepine-5(2H)—acetic acid | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any Examples 1 to 40 and 42.

EXAMPLE 46

1000 tablets each containing the following ingredients:

| | |
|---|---|
| [2S-[2α,5α(S)]]-5-[[3-(Benzoyl-amino)-2-oxo-4-phenylbutyl]-amino]dihydro-4-oxo-2-phenyl-2H—1,3-thiazine-3(4H)—acetic acid, monohydrochloride | 100 mg. |
| Avicel | 100 mg. |
| Hydrochlorothiazide | 12.5 mg. |
| Lactose | 113 mg. |
| Corn starch | 17.5 mg. |
| Stearic acid | 7 mg. |
| | 350 mg. | are prepared from sufficient bulk quantities by slugging the [2S-[2α,5α(S)]]-5-[[3-(benzoylamino)-2-oxo-4-phenylbutyl]amino]dihydro-4-oxo-2-phenyl-2H-1,3-thiazine-3(4H)-acetic acid, monohydrochloride, Avicel and a portion of the stearic acid. The slugs are ground and passed through a #2 screen, then mixed with the hydrochlorothiazide, lactose, corn starch, and the remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 42.

What is claimed is:

1. A compound of the formula

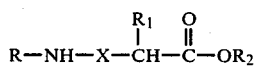

and a pharmaceutically acceptable salt thereof wherein

R is
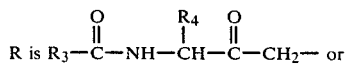
or
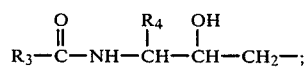

R₃ is
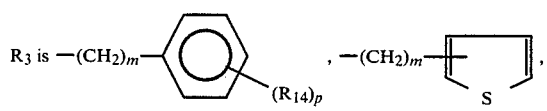
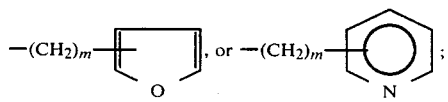

R₄ is hydrogen, lower alkyl,
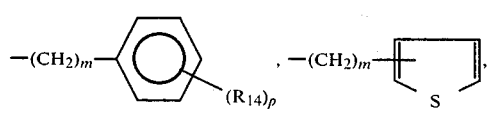
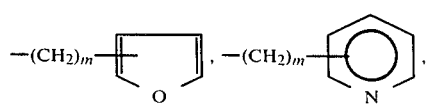

halo substituted lower alkyl, —(CH₂)ₘ—cycloalkyl,

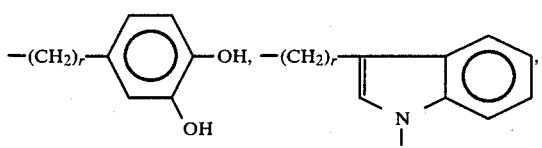

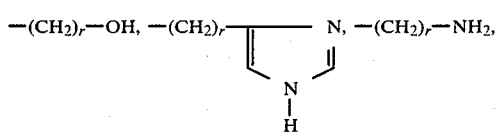

—(CH₂)ᵣ—SH, —(CH₂)ᵣ—S—lower alkyl,

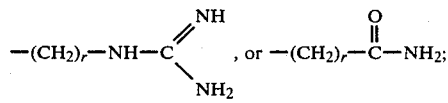

R₁₄ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two, three, or four;

p is one, two or three provided that p is more than one only if R₁₄ is hydrogen, methyl, methoxy, chloro, or fluoro;

r is one, two, three or four;

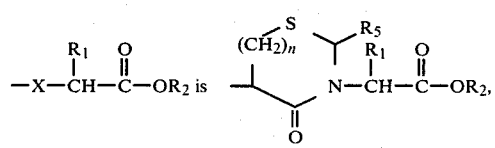

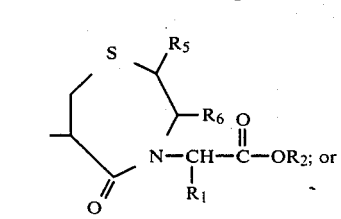

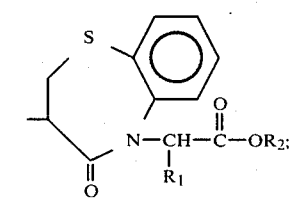

R₁ is hydrogen, lower alkyl, amino substituted lower alkyl, hydroxy substituted lower alkyl, or halo substituted lower alkyl;

n is one or two;

R₅ and R₆ are independently selected from the group consisting of hydrogen, lower alkyl, —(CH₂)ₘ—cycloalkyl and

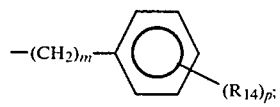

R₂ is hydrogen, lower alkyl, benzyl, benzhydryl, trimethylsilylethyl, salt forming ion, or

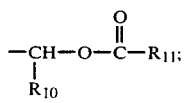

R₁₀ is hydrogen, lower alkyl, cycloalkyl or phenyl; and

R₁₁ is hydrogen, lower alkyl, lower alkoxy, cycloalkyl, phenyl, benzyl, or phenethyl.

2. A compound of claim 1 wherein:

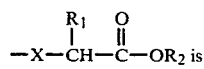

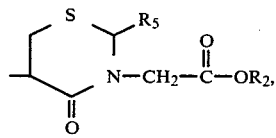

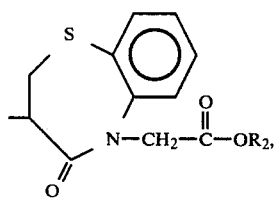

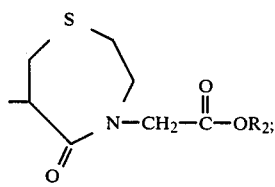

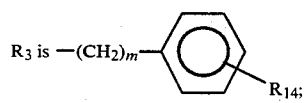

R₄ is straight or branched chain lower alkyl of 1 to 4 carbons, —(CH₂)ᵣ—NH₂,

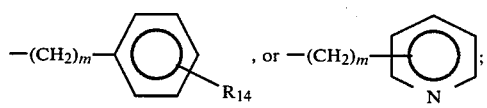

m is zero, one or two;

R₁₄ is hydrogen, methyl, methoxy, methylthio, Cl, Br, F or hydroxy;

r is an integer from 1 to 4;

R₅ is hydrogen or phenyl;

R₂ is hydrogen, alkali metal salt ion, or

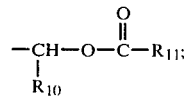

R₁₀ is hydrogen, straight or branched chain lower alkyl of 1 to 4 carbons, or cyclohexyl; and R₁₁ is straight or branched chain lower alkyl of 1 to 4 carbons.

3. A compound of claim 2 wherein:

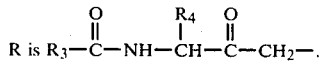

4. A compound of claim 3 wherein:

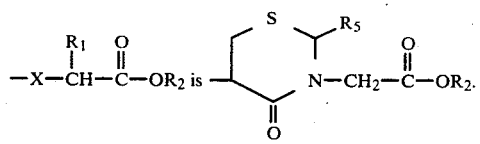

5. A compound of claim 4 wherein
R₃ is phenyl;
R₄ is benzyl;
R₅ is phenyl; and
R₂ is hydrogen.

6. The compound of claim 5, [2S-[2α,5α(S)]]-5-[[3-(benzoylamino)-2-oxo-4-phenylbutyl]amino]dihydro-4-oxo-2-phenyl-2H-1,3-thiazine-3(4H)-acetic acid, monohydrochloride.

7. A compound of claim 2 wherein:

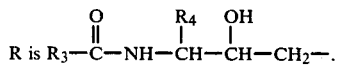

8. A compound of claim 7 wherein:

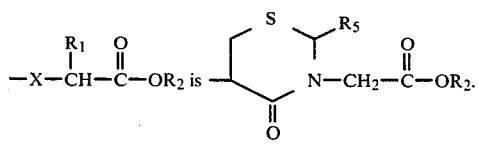

9. A compound of claim 8 wherein
R₃ is phenyl;
R₄ is benzyl;
R₅ is phenyl; and
R₂ is hydrogen.

10. A composition useful for treating hypertension comprising a pharmaceutically acceptable carrier and an effective amount of a hypotensive agent or pharmaceutically acceptable salt thereof of the formula

R—NH—X—CH(R₁)—C(O)—OR₂

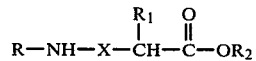

are as defined in claim 1.

11. A method of treating hypertension in a mammalian specie which comprises administering a hypotensively effective amount of the composition of claim 10.

* * * * *